(12) United States Patent
Hermann et al.

(10) Patent No.: US 8,670,032 B2
(45) Date of Patent: Mar. 11, 2014

(54) DEVICE AND METHOD FOR INSPECTING BOTTLES OR SIMILAR CONTAINERS

(75) Inventors: Jürgen Hermann, Rosenheim (DE); Horst Böcker, Schwerte (DE)

(73) Assignee: KHS GmbH, Dortmund (DE)

( * ) Notice: Subject to any disclaimer, the term of this patent is extended or adjusted under 35 U.S.C. 154(b) by 207 days.

(21) Appl. No.: 12/922,671

(22) PCT Filed: Mar. 18, 2009

(86) PCT No.: PCT/EP2009/001981
§ 371 (c)(1),
(2), (4) Date: Sep. 14, 2010

(87) PCT Pub. No.: WO2009/121482
PCT Pub. Date: Oct. 8, 2009

(65) Prior Publication Data
US 2011/0007148 A1    Jan. 13, 2011

(30) Foreign Application Priority Data
Apr. 3, 2008 (DE) .......................... 10 2008 017 427

(51) Int. Cl.
*H04N 7/18* (2006.01)
(52) U.S. Cl.
USPC ............................ 348/125; 348/127; 348/129
(58) Field of Classification Search
USPC .......................................... 348/125, 127, 129
See application file for complete search history.

(56) References Cited

U.S. PATENT DOCUMENTS

| | | | |
|---|---|---|---|
| 4,691,231 A | | 9/1987 | Fitzmorris et al. |
| 4,915,237 A | * | 4/1990 | Chang et al. .................. 209/524 |
| 5,045,688 A | * | 9/1991 | Domenico et al. ......... 250/223 B |
| 5,305,391 A | | 4/1994 | Gobibuchi |
| 6,049,379 A | * | 4/2000 | Lucas ........................ 356/240.1 |

FOREIGN PATENT DOCUMENTS

| | | |
|---|---|---|
| DE | 69128336 | 3/1998 |
| DE | 10140009 | 3/2003 |
| EP | 0 200 478 A | 11/1986 |
| EP | 0 415 154 A | 3/1991 |
| EP | 0 804 365 A | 11/1997 |
| JP | 04 350015 A | 12/1992 |
| WO | 03/016886 | 2/2003 |

\* cited by examiner

*Primary Examiner* — Chikaodili E Anyikire
(74) *Attorney, Agent, or Firm* — Occhiuti & Rohlicek LLP

(57) ABSTRACT

A container inspection device includes at least two cameras displaced from each other in a container's direction of travel and camera axes perpendicular to that direction. Each camera records an image of the same container region when the container is directly in front it. A difference between the images indicates a defect in form of the container. A device moves the container and records these images by some combination of rotating and/or pivoting. An electronic evaluation system compares the images and ascertains a defect in the form of the inspected container if they are different.

12 Claims, 2 Drawing Sheets

DEVICE AND METHOD FOR INSPECTING BOTTLES OR SIMILAR CONTAINERS

CROSS-REFERENCE TO RELATED APPLICATIONS

This application is the National Stage of International Application No. PCT/EP2009/001981, filed on Mar. 18, 2009, which claims the benefit of German Application Serial No. 10 2008 017 427.0, filed on Apr. 3, 2008, the contents of both of the foregoing applications are hereby incorporated by reference in their entirety.

The invention relates to a device for inspecting bottles and/or similar containers, in particular for detecting defects of form on containers according to the preamble of claim 1. In addition, the invention relates to a method for inspecting bottles or similar containers according to the preamble of claim 9.

An inspection device for, among other things, detecting contaminants, damage and other defects on bottles or similar containers is known. The known device comprises, among other things, a camera system formed by two cameras (CCD cameras), by way of which images of each bottle moved past the camera system on a transport section are generated from different viewing directions by means of a mirror arrangement with a plurality of mirrors in the beam path of the cameras and said images are evaluated in an evaluation unit for detecting contaminants or damage.

Also known is an inspection device (EP 0 804 365 B1) essentially comprising a detecting device in the form of a CCD camera, which is located at the side of a transport section, on which the empty bottles are moved past standing upright and rotating about their vertical axes.

It is the object of the invention to provide a device and a method for inspecting bottles or similar containers, for detecting possible defects in form of said containers. This object is achieved by a device corresponding to claim 1. A method for inspecting bottles or similar containers is the object of claim 9.

The device according to the invention, with a simplified structural embodiment and a higher level of operating reliability, enables dependable detecting of defects of form with a high output (number of containers passing the inspection device per unit time), in that at least two images of one and the same container region of each container are generated by way of at least one camera (in particular a CCD camera), wherein, between the recordings of the at least two images, the container is rotated or pivoted by an angular amount about an axis of rotation or a pivotal axis that, in the case of defect-free containers, is the container axis. The imaging of the respective container region is preferably effected, in this case, such that the optical axis of the camera or of the camera lens, i.e. the axis of recording, when recording the at least two images to be compared, in each case with reference to the axis of rotation or the pivotal axis, is rotated or pivoted about the relevant, preferably rotationally-symmetrical container, has in each case the same orientation and position and is preferably oriented in a radial manner in relation to the axis of rotation or pivotal axis. Through a simple comparison between the at least two images, a decision can be made as to the presence or absence of defects of form, i.e. whenever the at least two images are identical, this is a criterion for no defect of form. If the at least two images are different, it is a criterion showing that the relevant container has a defect of form.

Defects of form of the container in terms of the present invention are, among other things, deviations in the spacing between the wall surfaces and in this case in particular between the outside surface of the respective container and the axis of rotation or container axis, i.e., among other things, for example eccentricities or deviations from a rotationally-symmetrical form.

In the case of a preferred embodiment of the inspection device according to the invention, the containers are moved through the inspection device on a transport section, which is, for example, a linear or arcuate transport section, and, at the same time, rotated or pivoted about their container axis, are moved past at least two cameras of the camera system. The at least two cameras are provided one after the other in the direction of transport of the transport section such that they not only take two images of one and the same region of each container moved past the camera system and rotated about the container axis between the recordings, but the cameras are also additionally preferably located and controlled such that at the moment at which the at least two images are taken or generated, the recording axes of the cameras have the same orientation with reference to the axis of rotation or to the pivotal axis of the relevant container, i.e. for example they are oriented in a radial manner in relation to said axis of rotation. The rotating or revolving or pivoting of the containers on the transport section can be realized in the most varied ways.

It is also possible, in principle, to realize the inspection device such that the containers are moved in a pulsed manner through the inspection device or through an inspection position at that location, at which the at least two images of one and the same container region of each container are generated or recorded by way of a camera system, wherein each container is rotated or pivoted about an axis of rotation or a pivotal axis between the recordings and the orientation and position of the camera axis or recording axis, with reference to the axis of rotation or to the pivotal axis during the recordings, is identical. After the inspection, each container is moved on out of the inspection position.

Further developments, advantages and applications of the invention are produced from the following description of exemplary embodiments and from the Figures. In this case all features described and/or graphically represented are objects of the invention, either individually or in combination, irrespective of their summary in the claims or their dependency. The content of the claims is also made a component of the description.

The invention is described below by way of the Figures of an exemplary embodiment, in which, in detail:

Figure 1:
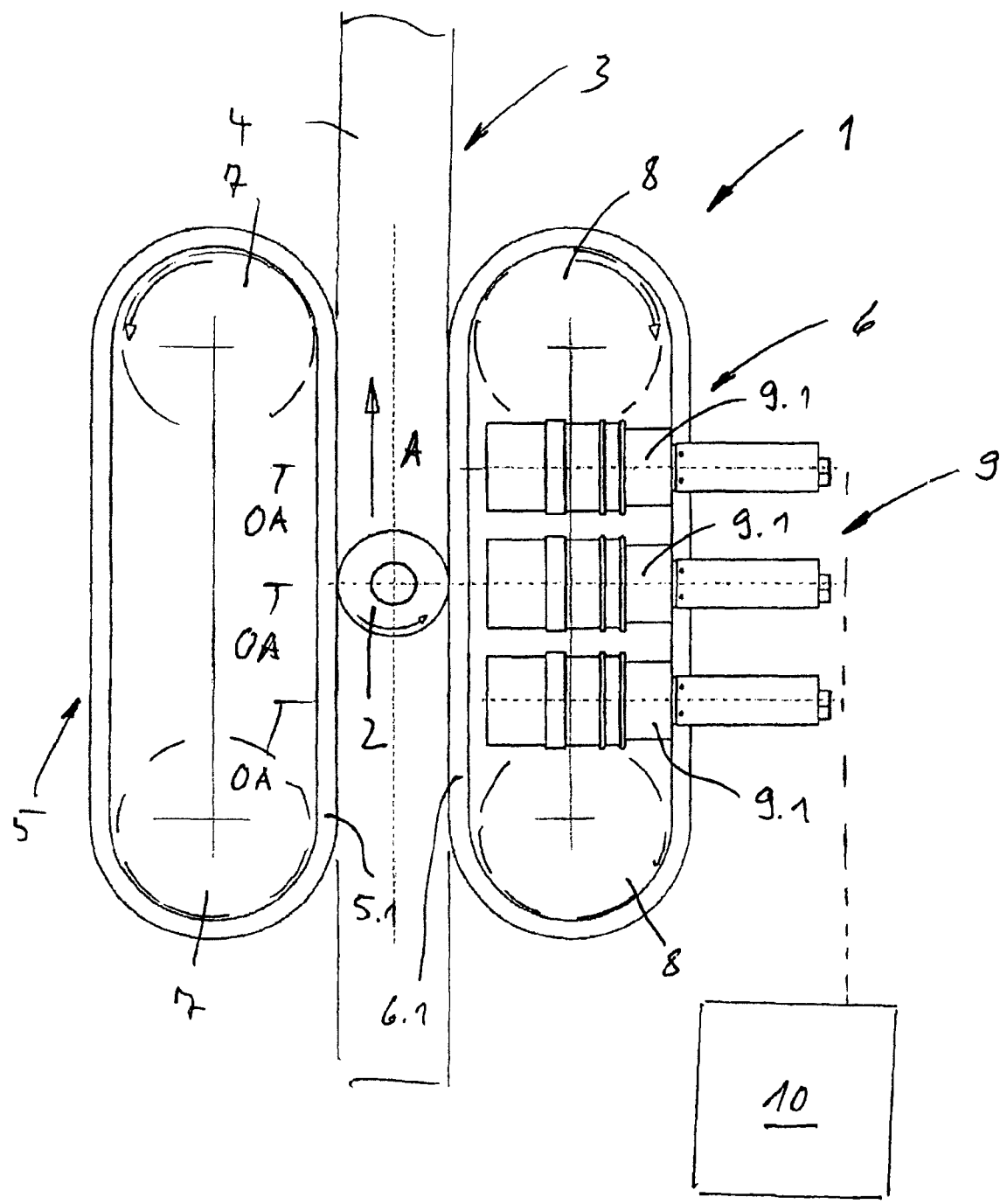
FIG. 1 shows a very simplified schematic representation of a top view of an inspection device for bottles or similar containers.
Figure 2:
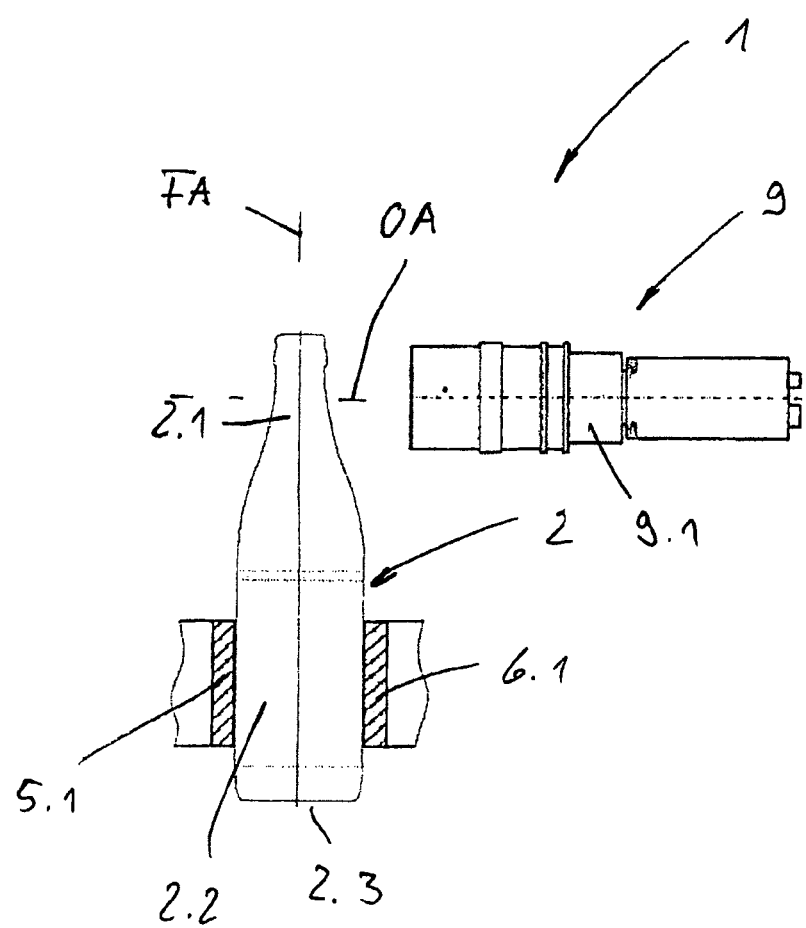
FIG. 2 shows a section corresponding to the line I-I in FIG. 1.

The device identified in general in FIG. 1 by the reference 1 is used for inspecting bottles 2, especially for detecting defects of form in the bottles 2 (out-of-roundness, eccentricities, deviations from a rotationally-symmetrical shape, etc.), in particular on the outside surface of the bottle.

The bottles 2 to be inspected are moved standing upright, i.e. with their bottle axis FA oriented in the vertical direction, in the direction of transport A through the device 1, in the form of a single-track flow on a transport section 4 that is formed by a conveyor 3. In the region of the device 1, the transport section 4 is defined at the side in each case by a length 5.1 or 6.1 of a belt 5 or 6 that for ms a closed loop and is driven in an endlessly circulating manner. The two belts are in each case guided via at least two guide wheels 7 or 8, which are oriented with their axes in the vertical direction and of which in each case one is driven in a circulating manner by a drive, in such a manner that the two belts 5 and 6, which are located with their loop planes in a common horizontal plane, move past the lengths 5.1 and 6.1 in the direction of transport A, though at different speeds.

By way of their lengths 5.1 and 5.2, the two belts 5 and 6 abut against the outside surface of the bottles 2 in the body region 2.2 of said bottles at a certain contact pressure such that through the different speeds of the belts 5 and 6, the bottles 2, standing upright by way of their bottle bottom 2.3 on the conveyor 3, are moved through the device 1 in each case rotating about a vertical axis of rotation.

A camera system 9 is provided in the device 1 on the transport section 4, said camera system, in the embodiment represented, being formed by a total of three CCD cameras 9.1, which are provided on one side of the transport section 4, in the embodiment represented above the belt 6, so as not to be entrained with said transport section. The cameras 9.1 are additionally provided with their camera axes or optical axes OA in a common horizontal plane, oriented vertically or transversely in relation to the direction of transport A and offset one in relation to another in the direction of transport in such a manner that at least one image of one and the same portion, for example the neck region 2.1, of each bottle 2 passing the device 1 is created by way of each camera 9.1. The cameras 9.1 are additionally positioned and focussed such that in each case they are at the same optical spacing from a vertical central plane of the transport section 4, which encloses the transport direction A and also the axis of rotation and the pivotal axis of the bottles 2, and also in each case detect the same image field. It is obvious that the cameras 9.1 have associated therewith an illuminating device that is not shown for the purposes of clarity.

The images generated by the cameras 9.1 are supplied as analogue image signals or as digital data sets to an evaluating and controlling unit 10, which is formed, for example, by a computer with suitable peripherals and in which the images of each bottle 2 generated by the cameras 9.1 are evaluated or processed using a program deposited in the evaluating and measuring unit 10.

As the bottles 2 are moved past the cameras 9.1 rotating about their vertical bottle axes FA on account of the different speeds of the belts 5 and 6, at least one image of each bottle reproducing the relevant bottle 2 or its bottle region in a different position of rotation is generated.

As the two belts 5 and 6 additionally abut against a relatively large area of the outside surface of the bottles 2 in the body region 2.2 by way of their lengths 5.1 and 6.1, the bottles 2 are rotated about the axis that is in the body region of said bottles. In the case of bottles 2 without defect of form, this axis of rotation is the bottle axis FA which the relevant bottle 2 also has outside the body region 2.2, i.e. for example at the bottle neck 2.1. In the case of bottles 2 with defects of form, the axis of rotation, i.e. the axis that such a bottle 2 has in the body region 2.1, can deviate completely from the axis in the region of the bottle neck 2.1.

The evaluation of the images is effected in accordance with the principle that whenever the images of a bottle recorded by way of the cameras 9.1 are identical or extensively identical, the relevant bottle 2 has no defect of form, at least in the region detected with the cameras 9.1, i.e. is realized rotationally-symmetrically or substantially rotationally-symmetrically in relation to the axis of rotation and also the bottle axis FA in the region detected by the cameras 9.1 (e.g. bottle neck 2.1) does not deviate from the axis of rotation or from the bottle axis in the body region 2.2.

If the images of one and the same bottle detected by the cameras 9.1 are different, this means that the relevant bottle has a defect in form, for example is out-of-round or eccentric and/or distorted in the region detected by the cameras 9.1, e.g. bottle neck 2.1, such that there is no continuous linear bottle axis between the bottle bottom 2.3 and the oppositely situated bottle mouth.

If a defect in form is ascertained on a bottle 2 and said defect in form is outside an admissible tolerance range, said defective bottle 2 is discharged, brought about, for example, by means of a corresponding signal from the evaluating and control unit 10.

The cameras 9.1 are controlled such that they generate in each case at least one image of each bottle 2 moved past, preferably such that the recording axis of said images is identical, with reference to the axis of rotation of the relevant container with regard to position and orientation, for example is radial in relation to the axis of rotation. The control of the cameras 9.1 is effected, for example, by means of sensor units (not shown in any more detail), which detect the moving of each bottle 2 past the respective camera 9.1.

It is obvious that by using the device 1 or a correspondingly adapted device, other containers, in particular also those with a form that is rotationally symmetrical in relation to the container axis, can be inspected or checked for possible defects of form in place of the bottles 2.

The invention has been described above by way of an exemplary embodiment. It is obvious that numerous changes and conversions are possible without in any way departing from the inventive concept underlying the invention.

Thus, it has been assumed above that the camera system 9 has a total of th ee cameras 9.1. The number of cameras used can obviously be different to this, however, in an expedient manner at least two cameras 9.1 detecting in each case one and the same region of the bottles 2 are provided.

In addition, it is possible to develop the camera system 9 with several groups of in each case at least two cameras 9.1, of which the cameras 9.1 of each group then in each case detect a certain region of the rotating or pivoting bottles 2 moved passed the cameras 9.1.

In addition, it has been assumed above that the rotating or pivoting movement of the bottles 2 is generated by two belts 5 and 6 circulating at different speeds. There are also obviously other possibilities for rotating or pivoting the bottles 2, for example by using rotating or pivoting bottle or container supports, on which or at which the bottles 2 are held.

LIST OF REFERENCES

1 Inspection device
2 Bottle
2.1 Bottle neck
2.2 Bottle body
2.3 Bottle bottom
3 Conveyor
4 Transport section
5, 6 Belt driven in a circulating manner
5.1, 6.1 Belt length
7, 8 Guide wheel
9.1 CCD camera
10 Evaluating and controlling unit
A Transport direction
FA Bottle axis
OA Optical axis

The invention claimed is:

1. An apparatus for inspecting containers, said containers, in absence of a defect in form, being at least one of rotationally symmetric to one of a rotational axis of said container and a pivotal axis of said container, said apparatus comprising a transport path for said containers along a direction of transport, said direction of transport and said rotational axis of said container defining a plane, a camera system for recording at least two images of a region of a container, said camera system comprising a first camera having a first camera axis that is perpendicular to said plane, and a second camera having a second camera axis that is perpendicular to said plane, said second camera being displaced from said first camera in said direction of transport, wherein said first camera is configured to record a first image, said first image being an image of a region of said container at an intersection of said plane and said first camera axis when said container is in front of said first camera, and wherein said second camera is configured to record a second image, said second image being an image of said region of said container at an intersection of said plane and said second camera axis when said container is in front of said second camera, whereby a difference between said first image and said second image is indicative of a defect in form of said container, a device for moving said container between recording of said first image and recording of said second image, wherein moving said container comprises at least one of rotating said container about said rotational axis and pivoting said container about said pivotal axis between recordation of said first image and said second image, and an electronic evaluation system for evaluating said first image and said second image, wherein said electronic evaluation system is configured for comparing said first image and said second image, and ascertaining a defect in form in said inspected container if said first image and said second image of said region of said container differ from one another.

2. The apparatus of claim 1, wherein said transport path advances said containers in front of said camera system along said direction of transport.

3. The apparatus of claim 1, wherein said cameras comprise at least one CCD camera.

4. The apparatus of claim 1, further comprising a control device for controlling said camera system in such a manner that said first image of said region is recorded at a first position of said container relative to said rotational axis and said second image of said is recorded at a second position of said container relative to said rotational axis, whereby in the absence of a defect in form, said first image would be identical to said second image and in the presence of a defect in form said second image would differ from said first image.

5. The apparatus of claim 1, wherein said camera system comprises at least a first group of cameras and a second group of cameras, wherein said first group of cameras comprises a first and second camera and said second group of cameras comprises a third and fourth camera, and wherein said first camera records said first image, said second camera record said first image, said third camera records said second image, and said fourth camera records said second image.

6. The apparatus of claim 1, wherein said device for moving said container between recording of said first image and recording of said second image comprises a first support surface for said container and a second support surface for said container, said first support surface being formed by a continuous revolving belt that can be driven at a first velocity, and said second support surface being formed by a continuous revolving belt that can be driven at a second velocity, wherein said second velocity is greater than said first velocity.

7. The apparatus of claim 1, wherein said device for moving said container between recording of said first image and recording of said second image comprises a rotating container carrier for a hanging configuration of said containers, wherein said rotating container carrier can be moved in a direction of transport.

8. The apparatus of claim 1, wherein said device for moving said container between recording of said first image and recording of said second image comprises a rotating container carrier for a standing configuration of said containers, wherein said rotating container carrier can be moved in a direction of transport.

9. The apparatus of claim 1, wherein said device for moving said container between recording of said first image and recording of said second image comprises a pivoting container carrier for a hanging configuration of said containers, wherein said pivoting container carrier can be moved in a direction of transport.

10. The apparatus of claim 1, wherein said device for moving said container between recording of said first image and recording of said second image comprises a pivoting container carrier for a standing configuration of said containers, wherein said pivoting container carrier can be moved in a direction of transport.

11. A method for inspecting containers for defects in form, said containers, in the absence of a defect in form, being rotationally symmetric about one of a rotational axis and a pivotal axis, said method comprising moving a container along a direction of transport, providing a camera system having a first camera, and a second camera offset from said first camera along said direction of transport, said first camera having a first camera axis perpendicular to a plane defined by said direction of transport and said rotational axis of said container, and said second camera having a second camera axis perpendicular to said plane, creating a first image of a region of said container when said container is in front of said first camera and said first camera axis intersects said region, moving said container after creating said first image, wherein moving comprises at least one of rotating said container about said rotational axis and pivoting said container about said pivotal axis, after having moved said container, creating a second image of said region of said container when said container is in front of said second camera and said second camera axis intersects said region, comparing said first image and said second image, and registering a defect in form in said container when said first image and said second image are different.

12. The method of claim 11, further comprising controlling said camera system in such a manner that said first image is recorded at a first position of said container relative to said rotational axis, and said second image is recorded at a second position of said container relative to said rotational axis, whereby in the absence of a defect in form, said first image and said second image would be identical and when a defect in form is present, said first image would differ from said second image.

* * * * *